United States Patent [19]

Schwede

[11] Patent Number: 4,608,077
[45] Date of Patent: Aug. 26, 1986

[54] PROCESS FOR PROMOTING AND REGULATING PLANT GROWTH WITH CAULERPIN

[76] Inventor: John G. Schwede, 875 56th Ave. South, St. Petersburg, Fla. 33705

[21] Appl. No.: 720,520

[22] Filed: Apr. 5, 1985

[51] Int. Cl.⁴ ............................................ A01N 43/38
[52] U.S. Cl. ............................................ 71/77; 71/96
[58] Field of Search ...................................... 71/96, 77

[56] References Cited

PUBLICATIONS

Hofinger et al., Chem. Abst., vol. 86 (1977) 134766p.

*Primary Examiner*—Catherine L. Mills
*Attorney, Agent, or Firm*—Walter J. Monacelli

[57] ABSTRACT

The compound caulerpin whose formula is given hereinafter and is derived from a marine alga has been found to have certain auxin-like properties for the stimulation of plant growth, either by itself or in combination with other auxins. Since standard bio-assay for auxin activity does not give positive results with caulerpin, this is regarded as a new type of plant growth regulator.

10 Claims, No Drawings

PROCESS FOR PROMOTING AND REGULATING PLANT GROWTH WITH CAULERPIN

BACKGROUND OF THE INVENTION

1. Field of the Invention

This invention relates to a new aid for the stimulation of plant growth. More specifically it pertains to the use of caulerpin as a growth promoter for various plants.

2. Description of the Prior Art

Caulerpin is a red crystalline substance derived from certain species of the marine alga Caulerpa and was first reported by Aguilar-Santos and Doty in a symposium on Aug. 27–29, 1967 at the University of Rhode Island. It is identified as dimethyl 5,12-dihydrocyclooctal (1,2-b : 5,6-b′) di-indole-6,13-dicarboxylate as was first determined by Maiti, Thomson and Mahendran and reported in the Journal of Chemical Research, 1978.

Various physical evidence attributes the formula to be:

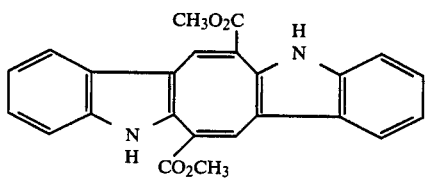

This is considered to be a dimer of indole-3-acrylic acid which has the formula:

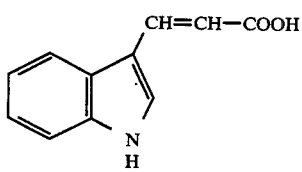

Careful search of the literature has found no suggestion of any activity of Caulerpin as a plant growth regulator or hormone.

Various methods of extracting Caulerpin from the powdered or whole alga Caulerpa have been described in the following publications: Aguilar-Santos, J. Chem. Soc. (C) 1970, pp. 842–3; the University of Rhode Island Symposium on "Drugs From The Sea", Aug. 22–29, 1967, (Ed. H. Freudenthal, Publ. of the Marine Technological Society, J. of Ocean Techn., (1968); Maiti, Thomson and Mahendran, J. Chem. Res. (s) pp. 126–7 and (m) pp. 1683–93 (1978); McConnell, Huges Targett, and Daley, J. Chem. Ecol. 8, 1437–51; Vest, Dawes and Romeo, Botanica Marina 26, 313–6 (1983); and Santos and Doty, Lloydia 34, 88–90 (1971). The test compound used hereinafter is derived by the method described in the above listed McConnell et al reference.

Among the indolic auxins, strong auxin activity has long been known to be associated with even number of carbon atoms in the side chain, e.g., indole-3-acetic acid, and indole-3-butyric acid and 2 and 4 C atoms respectively, while C3 side chains such as indole-3-propionic and indole-pyruvic acids show weaker activity in most tests (Thimann, K. V., 1972, Physiology of Development, The Hormones, in *Plant Physiology* Ed. F. C. Steward, Vol. VIB, Academic Press, New York). Unsaturation in the side chain is further associated with weakening of auxin effects. With regard to caulerpin the side chains which might carry chemical activity are cross-bonded to the indole nucleus reciprocally, such that they would be presumed inactive.

It is generally believed that the activity of natural auxins in plant growth is accompanied by production of ethylene, which has many physiological effects related to ripening of fruit, senescence, stress and wound responses, and to inhibition of root growth. Interaction of auxins and ethylene with other plant hormones is thought to achieve balance under normal conditions at various stages of growth and reproduction. Indeed, a number of auxin bio-assays, such as the cress root test, are based upon the ability of auxins to limit root growth when applied in moderate to high concentrations.

Hofinger, Archives Internationales de Physiologie et de Biochimie, 77, 225–30 (1969), reported indole-3-acrylic acid to be present in peas, lentils, and lupines (all members of the pea family Fabaceae), where it was thought to function as the principal auxin. The question of extraction artefact has subsequently arisen. Test results on lentil root sections, however, showed inhibition of growth in concentrations ranging down to $5 \times 10^{-7}$M, with slight stimulation in the order of 2–8% below that level, with effects disappearing at $10^{-9}$M. Hofinger, Gaspar, and Menard, (Comptes rendus, Acad. Sci. Paris, t. 290 (14 Ja., 1980) report stimulation of ethylene production in lentil roots in concentrations above $10^{-7}$M. and inhibition below this level to $10^{-9}$, the limit of activity.

Shimokawa, Phytochemistry, 22 1903–8 (1983), working with an ethylene forming enzyme obtained from *Citrus unshiu* (Satsuma orange), found that indole-3-acrylic acid non-competitively inhibited ethylene formation from 1-aminocyclopropane-1-carboxylic acid. However, in vivo, these results were not always reproduced. Endogenous ethylene production by apple tissue in vivo was not inhibited.

With reference to the marine environment, Augier has presented an exhaustive and definitive review of the subject of growth-active substances of marine plants (Botanica marine, 7 fascicles, 1976–78). However, neither indole-3-acrylic acid nor caulerpin is mentioned. Codomier, Segot and Teste (Botanica marine, 22:153-7, 1979) studied the effect of various phytohormones on the growth of *Asparagopsis armata* (marine alga, Rhodophyta). At $10^{-4}$M, indole-3-acrylic acid inhibited the growth of the crozier-like hooks of this species, but showed limited stimulation initially at $10^{-5}$ and $10^{-7}$M.

In certain cases potent auxins can overstimulate growth to the point of causing defoliation, or a herbicidal effect, or a stunting effect. For example, indole-3-acetic acid, beta-naphthoxyacetic acid and 2,4-dichlorophenoxyacetic acid can produce such effects.

SUMMARY OF THE INVENTION

In accordance with the present invention it has been found that caulerpin may be used to promote plant growth or regulation in some cases by itself and sometimes in combination with one or more other agents. This appears to be the first growth regulator to be derivable from a marine plant, namely from an alga. This compound has been found useful with cress and other agricultral plants or decorative plants with shoot growth and/or root growth. It is believed that the compound acts sometimes as an auxin in its own right and sometimes as an ethylene inhibitor. Thus applications may include retardation of fruit ripening and flower senescene, competitive inhibition of more potent auxins, such as herbicides and defoliants, and as an agricultural aid to inhibit ethylene production in water-logged soils.

In view of the limited solubility of caulerpin in water the tests for plant growth or regulation are conducted in the range of about $10^{-6}$ to $10^{-9}$ gram per ml. which translates to about 0.001–1 mg. per liter, preferably about $10^{-7}$ or 0.1 mg. per liter. Since Caulerpin has a molecular weight of 398 (roughly 400) the molar concentration can be derived by multiplying the mg/liter by 2.5. Thus $10^{-6}$ concentration represents $2.5 \times 10^{-6}$M.

Although the stimulatory effect of Caulerpin on root and shoot growth in seedlings shows some features in common with auxins, the standard and usual bio-assay tests for auxins, such as oat coleoptile straight growth test, bean stem curvature test, split pea stem and pea section tests, and tomato epinasty have shown no significant auxin activity. Whereas root inhibition is expected with auxin in the cress root test, Caulerpin shows potent stimulation. Root stimulation generally is well above the level expected with standard auxins in many plants. By reason of this pattern, Caulerpin is regarded as a new and distant type of auxin. This novelty is supported by its dimeric structure, not otherwise known among auxins, and its origin from a marine alga, no novel or unique auxin having been previously known from this group of sea plants.

PROCEDURE FOR TESTING THE EFFECT OF CAULERPIN ON GERMINATION AND SEEDLING GROWTH

Depending on seed size, a suitable number of seeds are placed on filter paper in standard Petri dishes and moistened with 5 ml. of deionized water as control. Germinations are carried out at ambient indoor temperature in the dark by placing the Petri dishes in porous cardboard containers together with an open water-filled tray to maintain humidity in a closed, dark space. However, temperature and humidity are not further controlled. With most vegetable seeds, this method produces seedlings suitable for measurement in 3–4 days. These are generally inspected daily.

Although it is possible in most cases to measure root and shoot growth separately, in some plants these are not readily distinguished at an early stage, in which case total linear growth external to seed coat is measured. Measurements are carried out as rapidly as possible to the nearest millimeter, employing head magnifier and transparent ruler, since in many cases serial observations are intended. Since radicle protrusion as a result of water inhibition is the first stage of germination prior to true growth in most seeds, seeds at this stage are included in germination totals but are not calculated into averages. The determinations are represented by the following symbols:

$N_t$ = Total number of seeds employed
G = Percent germinated, including evidence of radicle protrusion.
R = Mean root length
S = Mean shoot length
M = Percent measurable (excludes those with radicle protrusion only)
Per = Period of test.

Measurements are reported in millimeters (mm). Concentrations are given in grams per milliliter (g/ml). Thus $10^{-6}$ represents 1.0 mg/liter.

SPECIFIC EMBODIMENTS OF THE INVENTION

The invention is illustrated by the following examples which are intended merely for purpose of illustration and are not to be regarded as limiting the scope of the invention or the manner in which it may be practiced. Unless specifically indicated otherwise, parts and percentages are given by weight.

EXAMPLE I

A number of tests are performed as described above with the number of seeds employed ($N_t$), percent germinated (G), percent measurable (M), mean root length (R), mean shoot length (S), period of test (Per.) and percent increase over control (% Incr.) as shown in the table below

TABLE I

| Exp. No. | Seed | Per. | CONTROL $N_t$ | G (%) | M (%) | R | S | CAULERPIN Conc. | $N_t$ | G (%) | M (%) | R | S | % Incr. R | S |
| --- | --- | --- | --- | --- | --- | --- | --- | --- | --- | --- | --- | --- | --- | --- | --- |
| 1 | Cress | 9 hrs. | 13 | 100 | 100 | 15.3 | — | $10^{-7}$ | 20 | 100 | 100 | 26.0 | — | 70 | — |
| 2 | Cress | 9 hrs. | " | " | " | " | — | $10^{-8}$ | 16 | 100 | 100 | 26.2 | — | 71 | — |
| 3 | Cress | 9 hrs. | " | " | " | " | — | $10^{-9}$ | 25 | 100 | 100 | 27.9 | — | 82 | — |
| 4 | Cress | 17 hrs. | 14 | 100 | 100 | 16.4 | 6.0 | $10^{-9}$ | 13 | 100 | 100 | 18.9 | 6.3 | 15 | 5 |
| 5 | Peas Alaska | 3 days | 8 | 63 | 63 | 9.0 | 0 | $10^{-7}$ | 8 | 100 | 100 | 33.8 | 1.3 | 276 | — |
| 6 | Oats Terra | 3.5 days | 17 | 76 | 76 | 14.5 | 8.1 | $10^{-7}$ | 22 | 50 | 50 | 21.6 | 10 | 49 | 23 |
| 7 | Cucumber | 3 days | 10 | 100 | 100 | 46.2 | 13.0 | $10^{-7}$ | 12 | 100 | 100 | 49.3 | 18.2 | 7 | 40 |
| 8 | Radish Spark. | 4 days | 18 | 100 | 100 | 61.7 R+S | 29.8 | $10^{-7}$ | 30 | 100 | 100 | 75.4 R+S | 25.4 R+S | 22 | — |
| 9 | Carrot Dan. | 4 days | 26 | 100 | 100 | 6.1 | | $10^{-7}$ | 21 | 100 | 100 | 11.1 | | 82 | — |
| 10 | Cucumber | 3 days | 13 | 100 | 85 | 26.5 | 3.6 | $10^{-7}$ | 13 | 85 | 85 | 29.2 | 5.6 | 10 | 55 |
| 11 | Mustard | 3 days | 23 | 61 | 61 | 12.1 | 6.7 | $10^{-7}$ | 24 | 42 | 42 | 23.9 | 11.1 | 98 | 66 |

EXAMPLE II

Lentils, Oregon

The procedure of Example I is repeated using lentil seed with the conditions and results as listed in Table II.

TABLE II

| Test Period | CONTROL | | | | | CAULERPIN ($10^{-9}$) | | | | | % Incr. | |
|---|---|---|---|---|---|---|---|---|---|---|---|---|
| | $N_t$ | G (%) | M (%) | Root | Shoot | $N_t$ | G (%) | M (%) | Root | Shoot | Root | Shoot |
| 2 days | 13 | 92 | 85 | 11.6 | 5.9 | 13 | 100 | 100 | 15.3 | 8.5 | 32 | 44 |
| 3 days | 19 | 92 | 85 | 21.2 | 16.3 | 13 | 100 | 100 | 35.5 | 20.5 | 68 | 26 |

EXAMPLE III

Cabbage (Premium Late Flat Dutch)

The procedure of Example I is repeated using cabbage seed with the conditions and results as listed in Table III.

TABLE III

| Test Period | CONTROL | | | | | CAULERPIN ($10^{-9}$) | | | | | % Incr. | |
|---|---|---|---|---|---|---|---|---|---|---|---|---|
| | $N_t$ | G (%) | M (%) | Root | Shoot | $N_t$ | G (%) | M (%) | Root | Shoot | Root | Shoot |
| 4 days | 18 | 72 | 33 | 26.7 | 17.3 | 16 | 83 | 33 | 34.0 | 15.7 | 27 | −9 |

EXAMPLE IV

Mustard

The procedure of Example I is repeated using mustard seed with the conditions and results as listed in Table IV.

TABLE IV

| Test Period | CONTROL | | | | | CAULERPIN ($10^{-9}$) | | | | | % Incr. | |
|---|---|---|---|---|---|---|---|---|---|---|---|---|
| | $N_t$ | G (%) | M (%) | Root | Shoot | $N_t$ | G (%) | M (%) | Root | Shoot | Root | Shoot |
| 3 days | 22 | 86 | 73 | 20.4 | 18.9 | 20 | 75 | 65 | 26.4 | 20.7 | 29 | 10 |

EXAMPLE V

Mustard

The procedure of Example V is repeated using a mixture of Caulerpin and indole-acrylic acid ($10^{-6}$ each) with the conditions and results as listed in Table V.

TABLE V

| Test Period | CONTROL | | | | | CAULERPIN ($10^{-6}$) | | | | | % Incr. | |
|---|---|---|---|---|---|---|---|---|---|---|---|---|
| | $N_t$ | G (%) | M (%) | Root | Shoot | $N_t$ | G (%) | M (%) | Root | Shoot | Root | Shoot |
| 3 days | 22 | 86 | 73 | 20.4 | 18.9 | 20 | 85 | 80 | 29.6 | 23.5 | 45 | 24 |

EXAMPLE VI

Beefsteak Tomato

The procedure of Example I is repeated using beefsteak tomato seed with the conditions and results as listed in Table VI.

TABLE VI

| Test Period | CONTROL | | | | | CAULERPIN ($10^{-6}$) | | | | | % Incr. | |
|---|---|---|---|---|---|---|---|---|---|---|---|---|
| | $N_t$ | G (%) | M (%) | Root | Shoot | $N_t$ | G (%) | M (%) | Root | Shoot | Root | Shoot |
| 3 days | 28 | 79 | 79 | 20.2 | 6.5 | 27 | 100 | 100 | 22.1 | 8.7 | 9 | 34 |

EXAMPLE VII

Rutabaga

The procedure of Example I is repeated using Rutabaga seed with the conditions and results as listed in Table VII.

TABLE VII

| Test Period | CONTROL | | | | | CAULERPIN ($10^{-8}$) | | | | | % Incr. | |
|---|---|---|---|---|---|---|---|---|---|---|---|---|
| | $N_t$ | G (%) | M (%) | Root | Shoot | $N_t$ | G (%) | M (%) | Root | Shoot | Root | Shoot |
| 3 days | 28.0 | 90 | 81 | 28.0 | 14.1 | 17 | 100 | 100 | 30.7 | 12.4 | 10 | −12 |

EXAMPLE VIII

Rutabaga

The Procedure of Example I is repeated using indole acetic acid in place of the Caulerpin for comparison with the conditions and results as listed in Table VIII.

TABLE VIII

| Test Period | CONTROL | | | | | Indole Acetic acid ($10^{-7}$) | | | | | % Incr. | |
|---|---|---|---|---|---|---|---|---|---|---|---|---|
| | $N_t$ | G (%) | M (%) | Root | Shoot | $N_t$ | G (%) | M (%) | Root | Shoot | Root | Shoot |
| 3 days | 28.0 | 90 | 81 | 28.0 | 14.1 | 15 | 87 | 87 | 34.7 | 11.6 | 24 | −18 |

EXAMPLE IX

Rutabaga

The procedure of Example I is repeated using a combination of Caulerpin ($5 \times 10^{-7}$) and Seaborn extract (1:500) with the conditions and results as listed in Table IX.

TABLE IX

| Test | CONTROL | | | | | CAULERPIN + SBE | | | | | % Incr. | |
|---|---|---|---|---|---|---|---|---|---|---|---|---|
| Period | $N_t$ | G (%) | M (%) | Root | Shoot | $N_t$ | G (%) | M (%) | Root | Shoot | Root | Shoot |
| 3 days | 28.0 | 90 | 81 | 28.0 | 14.1 | 18 | 89 | 89 | 37.3 | 16.4 | 33 | 16 |

EXAMPLE X

Okra

The procedure of Example I is repeated using okra seed with the conditions and results as listed in Table X.

TABLE X

| Test | CONTROL | | | | | CAULERPIN ($10^{-8}$) | | | | | % Incr. | |
|---|---|---|---|---|---|---|---|---|---|---|---|---|
| Period | $N_t$ | G (%) | M (%) | Root | Shoot | $N_t$ | G (%) | M (%) | Root | Shoot | Root | Shoot |
| 3 days | 11 | 100 | 100 | 17.6 | 6.4 | 11 | 90 | 90 | 22.8 | 9.0 | 30 | 41 |

EXAMPLE XI

Radish

The procedure of Example I is repeated using radish seed with the conditions and results as listed in Table XI.

TABLE XI

| Test | CONTROL | | | | | CAULERPIN ($10^{-6}$) | | | | | % Incr. | |
|---|---|---|---|---|---|---|---|---|---|---|---|---|
| Period | $N_t$ | G (%) | M (%) | Root | Shoot | $N_t$ | G (%) | M (%) | Root | Shoot | Root | Shoot |
| 3 days | 12 | 100 | 100 | 47.9 | 13.3 | 14 | 93 | 93 | 68.9 | 16.8 | 44 | 26 |

EXAMPLE XII

Turnip (Seven Top)

The Procedure of Example I is repeated using turnip seed with the conditions and results as listed in Table XII.

TABLE XII

| Test | CONTROL | | | | | CAULERPIN ($2 \times 10^{-7}$) | | | | | % Incr. | |
|---|---|---|---|---|---|---|---|---|---|---|---|---|
| Period | $N_t$ | G (%) | M (%) | Root | Shoot | $N_t$ | G (%) | M (%) | Root | Shoot | Root | Shoot |
| 3 days | 15 | 93 | 98 | 39.7 | 22.5 | 16 | 94 | 94 | 56.6 | 29.3 | 43 | 30 |

EXAMPLE XIII

Sea Oats (*Uniola paniculata*)

The procedure of Example I is repeated using sea oats seed with the conditions and results as listed in Table XIII.

TABLE XIII

| Test | CONTROL | | | | | CAULERPIN ($10^{-6}$) | | | | | % Incr. | |
|---|---|---|---|---|---|---|---|---|---|---|---|---|
| Period | $N_t$ | G (%) | M (%) | Root | Shoot | $N_t$ | G (%) | M (%) | Root | Shoot | Root | Shoot |
| 11 days | 30 | 50 | 47 | 42.3 | 26.7 | 28 | 46 | 46 | 54.5 | 30.7 | 29 | 15 |

Seedlings transplanted to outside flats had survival rate and appeared more vigorous than controls, with watering with Caulerpin solution ($10^{-6}$) being continued for two weeks.

EXAMPLE XIV

Chard

The procedure of Example I is repeated in three replicates using chard seed with the conditions and averaged results as listed in Table XIV.

TABLE XIV

| Test | CONTROL | | | | CAULERPIN ($10^{-8}$) | | | | % Incr. |
|---|---|---|---|---|---|---|---|---|---|
| Period | $N_t$ | G (%) | M (%) | Root + Shoot | $N_t$ | G (%) | M (%) | Root + Shoot | Root + Shoot |
| 3 days | 45 | 33 | 33 | 6.1 | 51 | 22 | 22 | 12.0 | 97 |
| 7 days | 45 | 71 | 67 | 28.3 | 51 | 39 | 39 | 46.2 | 63 |

EXAMPLE XV

Spinach

The procedure of Example XIV is repeated using spinach seed with the conditions and averaged results as listed in Table XV.

TABLE XV

| Test Period | CONTROL $N_t$ | G (%) | M (%) | Root + Shoot | CAULERPIN ($10^{-6}$) $N_t$ | G (%) | M (%) | Root + Shoot | % Incr. Root + Shoot |
|---|---|---|---|---|---|---|---|---|---|
| 5 days | 59 | 12 | 8 | 21.0 | 60 | 28 | 22 | 33.8 | 61 |
| 9 days | 50 | 19 | 19 | 39.6 | 60 | 47 | 38 | 58.3 | 47 |

EXAMPLE XVI

Spinach

The procedure of Example XIV is repeated using spinach seed with the conditions and averaged results as listed in Table XVI.

TABLE XVI

| Test Period | CONTROL $N_t$ | G (%) | M (%) | Root + Shoot | CAULERPIN ($10^{-7}$) $N_t$ | G (%) | M (%) | Root + Shoot | % Incr. Root + Shoot |
|---|---|---|---|---|---|---|---|---|---|
| 5 days | 59 | 12 | 8 | 21.0 | 80 | 39 | 29 | 23.8 | 13 |
| 9 days | 59 | 19 | 19 | 39.6 | 80 | 52 | 45 | 58.8 | 48 |

EXAMPLE XVII

Spinach

The procedure of Example XIV is repeated using spinach seed with the conditions and averaged results as listed in Table XVII.

TABLE XVII

| Test Period | CONTROL $N_t$ | G (%) | M (%) | Root + Shoot | Indole Acrylic Acid CAULERPIN (Each $10^{-6}$) $N_t$ | G (%) | M (%) | Root + Shoot | % Incr. Root + Shoot |
|---|---|---|---|---|---|---|---|---|---|
| 9 days | 59 | 19 | 19 | 39.6 | 60 | 28 | 25 | 64.5 | 63 |

EXAMPLE XVIII

Chard

The procedure of Example XIV is repeated using chard seed with the conditions and averaged results as listed in Table XVIII.

TABLE XVIII

| Test Period | CONTROL $N_t$ | G (%) | M (%) | Root + Shoot | CAULERPIN ($10^{-9}$) $N_t$ | G (%) | M (%) | Root + Shoot | % Incr. Root + Shoot |
|---|---|---|---|---|---|---|---|---|---|
| 7 days | 45 | 71 | 67 | 28.3 | 51 | 56 | 56 | 53.8 | 90 |

EXAMPLE XIX

Cucumber

The procedure of Example XIV is repeated using cucumber seed with the conditions and averaged results as listed in Table XIX.

TABLE XIX

| Test Period | CONTROL $N_t$ | G (%) | M (%) | Root | Shoot | CAULERPIN ($10^{-8}$) $N_t$ | G (%) | M (%) | Root | Shoot | % Incr. Root | Shoot |
|---|---|---|---|---|---|---|---|---|---|---|---|---|
| 7 days | 43 | 81 | 63 | 31.6 | 9.6 | 44 | 68 | 41 | 39.4 | 8.3 | 25 | −14 |

EXAMPLE XX

Tomato

The procedure of Example XIV is repeated using tomato seed with the conditions and averaged results as listed in TABLE XX.

TABLE XX

| Test Period | CONTROL $N_t$ | G (%) | M (%) | Root | Shoot | CAULERPIN $N_t$ | G (%) | M (%) | Root | Shoot | % Incr. Root | Shoot |
|---|---|---|---|---|---|---|---|---|---|---|---|---|
| 5 days | 79 | 91 | 90 | 29.3 | 7.8 | 61 | 95 | 93 | 33.3 | 11.1 | 14 | 42 |

EXAMPLE XXI

Tomato

The procedure of Example XIV is repeated using tomato seed with the conditions and averaged results as listed in Table XXI.

TABLE XXI

| Test | CONTROL | | | | | Indole Acrylic Acid + CAULERPIN ($10^{-6}$ each) | | | | | % Incr. | |
|---|---|---|---|---|---|---|---|---|---|---|---|---|
| Period | $N_t$ | G (%) | M (%) | Root | Shoot | $N_t$ | G (%) | M (%) | Root | Shoot | Root | Shoot |
| 5 days | 79 | 91 | 90 | 29.3 | 7.8 | 57 | 96 | 96 | 35.3 | 9.7 | 20 | 24 |

EXAMPLE XXII

Eggplant

The procedure of Example XIV is repeated using eggplant seed with the conditions and averaged results as listed in Table XXII.

TABLE XXII

| Test | CONTROL | | | | | CAULERPIN ($10^{-7}$) | | | | | % Incr. | |
|---|---|---|---|---|---|---|---|---|---|---|---|---|
| Period | $N_t$ | G (%) | M (%) | Root | Shoot | $N_t$ | G (%) | M (%) | Root | Shoot | Root | Shoot |
| 13 days | 45 | 64 | 64 | 11.6 | 7.3 | 46 | 56 | 56 | 24.6 | 15.2 | 112 | 108 |

EXAMPLE XXIII

Corn (Golden Bantam)

The procedure of Example XIV is repeated using corn seed with the conditions and averaged results as listed in Table XXIII.

TABLE XXIII

| Test | CONTROL | | | | | CAULERPIN ($10^{-6}$) | | | | | % Incr. | |
|---|---|---|---|---|---|---|---|---|---|---|---|---|
| Period | $N_t$ | G (%) | M (%) | Root | Shoot | $N_t$ | G (%) | M (%) | Root | Shoot | Root | Shoot |
| 4 days | 24 | 83 | 83 | 16.7 | * | 24 | 96 | 96 | 24.6 | * | 147 | — |

\* — Shoot not sufficiently advanced to measure

EXAMPLE XXIV

Corn (Golden Bantam)

The procedure of Example XIV is repeated using corn seed with the conditions and averaged results as listed in Table XXIV.

TABLE XXIV

| Test | CONTROL | | | | | Indole Acrylic Acid + CAULERPIN ($10^{-7}$) | | | | | % Incr. | |
|---|---|---|---|---|---|---|---|---|---|---|---|---|
| Period | $N_t$ | G (%) | M (%) | Root | Shoot | $N_t$ | G (%) | M (%) | Root | Shoot | Root | Shoot |
| 4 days | 24 | 83 | 83 | 16.7 | * | 24 | 100 | 100 | 28.8 | * | 72 | — |

\* — Shoot not sufficiently advanced to measure

EXAMPLE XXV

Sunflower

The procedure of Example XIV is repeated using sunflower seed with the conditions and averaged results as listed in Table XXV.

TABLE XXV

| Test | CONTROL | | | | | CAULERPIN ($10^{-6}$) | | | | | % Incr. | |
|---|---|---|---|---|---|---|---|---|---|---|---|---|
| Period | $N_t$ | G (%) | M (%) | Root | Shoot | $N_t$ | G (%) | M (%) | Root | Shoot | Root | Shoot |
| 6 days | 18 | 89 | 72 | 27.3 | 11.2 | 18 | 94 | 94 | 40.9 | 15.3 | 50 | 37 |

EXAMPLE XXVI

Geranium

The procedure of Example XIV is repeated using geranium seed with the conditions and averaged results as listed in Table XXVI.

TABLE XXVI

| Test | CONTROL | | | | | CAULERPIN ($10^{-6}$) | | | | | % Incr. | |
|---|---|---|---|---|---|---|---|---|---|---|---|---|
| Period | $N_t$ | G (%) | M (%) | Root | Shoot | $N_t$ | G (%) | M (%) | Root | Shoot | Root | Shoot |
| 4 days | 37 | 70 | 51 | 14.8 | 22.9 | 35 | 74 | 34 | 19.5 | 24.8 | 32 | 8 |

EXAMPLE XXVII

Squash (Crookneck)

The procedure of Example XIV is repeated using squash seed with the conditions and averaged results as listed in Table XXVII.

TABLE XXVII

| Test | CONTROL | | | | | Indole Acrylic Acid + CAULERPIN ($10^{-6}$) | | | | | % Incr. | |
|---|---|---|---|---|---|---|---|---|---|---|---|---|
| Period | $N_t$ | G (%) | M (%) | Root | Shoot | $N_t$ | G (%) | M (%) | Root | Shoot | Root | Shoot |
| 7 days | 24 | 83 | 83 | 50.4 | 17.6 | 31 | 94 | 94 | 63.8 | 24.2 | 27 | 38 |

SUMMARY OF TEST RESULTS

The effect of the presence of Caulerpin may vary with the plant species. Effects are more notable on root growth than on shoot growth. However either may respond to caulperin with increased growth. Plants known to be high ethylene producers generally respond with root elongation.

The above test results with Caulerpin on concentrations between 0.01 and 1 mg/liter may be tabulated as follows:

| | Percent Increase Over Control | | |
|---|---|---|---|
| Plant Seed | Root Growth | Shoot Growth | Root + Shoot Growth |
| Eggplant | 112 | 108 | |
| Chard | | | 90 |
| Lentil | 68 | 26 | |
| Spinach | | | 60 |
| Sunflower | 50 | 37 | |
| Corn | 47 | | |
| Sea Oats | 28 | 15 | |

With a mixture of Caulerpin and indole acrylic acid, using 1.0 mg.L of each, the percent increases over control are:

| | Root Growth (% Incr.) |
|---|---|
| Squash | 27 |
| Mustard | 45 |
| Spinach | 62 |
| Tomato | 20 |

There does not appear to be any overall correlation of increased germination rate with Caulerpin growth response. In a few instances, for example, with chard, Caulerpin appears to decrease germination while still promoting growth. In general, however, it may be observed that seed of poorer quality or greater age may be enhanced with Caulerpin, while vigorous seedlings from seeds of high germination rate are less likely to show quantitative effects from external chemical influences of any sort.

Synthetic auxins such as 2,4-dichlorophenoxyacetic acid and indol-3-acetic acid which act as herbicides and defoliants by virtue of excessive auxin-type stimulation to a lethal level, show extreme root inhibition in low concentrations in tests of the type utilized here, producing stubby, nubbin-like, stunted root formations. In concentrations of 1 mg/liter of Caulerpin with similar amounts respectively of the 2,4-D or the indole-3-acetic acid this stunting effect is lessened with some root elongation in most plant species tested.

In the case of sea oats (*Uniola paniculata*), a coastal plant which stabilizes dunes in Florida, tests indicate promotion of root growth by Caulerpin. Planting of laboratory-germinated seedlings to outdoor flats accompanied by watering with Caulerpin ($10^{-6}$ concentration in deionized water) over the first two weeks has produced plants which generally show increased height and vigor, as compared with controls, over a two month period.

While certain features of this invention have been described in detail with respect to various embodiments thereof, it will of course be apparent that other modifications can be made within the spirit and scope of this invention and it is not intended to limit the invention to the exact details shown above except insofar as they are defined in the following claims.

The invention claimed is:

1. The method of promoting plant growth comprising the step of treating the plant seed intimately and continuously with an aqueous solution containing 0.001–1 milligrams of Caulerpin per liter of solution for a period of at least one day.

2. The method of claim 1 in which said concentration is in the range of 0.01–1 milligrams per liter.

3. The method of claim 1 in which said concentration is about 0.1 milligram per liter.

4. The method of claim 1 in which said treatment is for a period of at least two days.

5. The method of claim 1 in which said treat is for a period of at lest three days.

6. The method of claim 1 in which said plant seed is selected from the class consisting of chard, corn, cucumber, eggplant, lentil, sea oats, spinach and sunflower seeds.

7. The method of claim 6 in which the concentration of said Caulerpin in said solution is 0.01–1 milligram per liter.

8. The method of claim 7 in which said treatment is for a period of at least three days.

9. The method of claim 8 in which said concentration is about 0.1 milligram per liter.

10. The method of any one of claims 7, 8 or 9, in which said plant seed is selected from the class consisting of squash, mustard, spinach and tomato seeds.

* * * * *

UNITED STATES PATENT AND TRADEMARK OFFICE
CERTIFICATE OF CORRECTION

PATENT NO.  : 4,608,077
DATED       : August 26, 1986
INVENTOR(S) : JOHN G. SCHWEDE It is certified that error appears in the above-identified patent and that said Letters Patent is hereby corrected as shown below:

On the title page:

Correct the inventor's address to read:

--- 6795 23rd Street South
    St. Petersburg, Florida 33712 ---

Col. 3, line 23, correct "distant" to read ---distinct---.

Col. 4, line 6, correct "inhibition" to read ---imbibition---.

Col. 14, line 33, correct "treat" to read ---treatment---.

Col. 14, line 34, correct "lest" to read ---least---.

Signed and Sealed this

Second Day of December, 1986

*Attest:*

DONALD J. QUIGG

*Attesting Officer*       *Commissioner of Patents and Trademarks*